(12) United States Patent
Subramaniam

(10) Patent No.: US 8,941,057 B2
(45) Date of Patent: Jan. 27, 2015

(54) PROBE AND METHOD FOR OBTAINING THREE-DIMENSIONAL COMPOSITIONAL MAPS OF A BIOLOGICAL SAMPLE

(75) Inventor: Sriram Subramaniam, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1336 days.

(21) Appl. No.: 12/676,861

(22) PCT Filed: Sep. 4, 2008

(86) PCT No.: PCT/US2008/075224
§ 371 (c)(1),
(2), (4) Date: Oct. 5, 2010

(87) PCT Pub. No.: WO2009/032904
PCT Pub. Date: Mar. 12, 2009

(65) Prior Publication Data
US 2011/0011190 A1     Jan. 20, 2011

Related U.S. Application Data

(60) Provisional application No. 60/970,070, filed on Sep. 5, 2007, provisional application No. 60/974,686, filed on Sep. 24, 2007.

(51) Int. Cl.
*G01D 21/00*     (2006.01)
*H01J 49/00*     (2006.01)
(Continued)

(52) U.S. Cl.
CPC ........ *G01N 33/6848* (2013.01); *G01N 33/5082* (2013.01); *H01J 37/28* (2013.01);
(Continued)

(58) Field of Classification Search
CPC ..... B82Y 35/00; G01N 33/6848; H01J 37/28; H01J 37/3053; H01J 49/0004; H01J 49/0459; H01J 49/0404
USPC ................. 250/288, 282; 73/866.5; 850/62, 5
See application file for complete search history.

(56) References Cited

U.S. PATENT DOCUMENTS 5,440,122 A * 8/1995 Yasutake .................... 250/443.1
5,444,260 A * 8/1995 Kazmerski ................. 250/492.3
(Continued)

FOREIGN PATENT DOCUMENTS

WO    WO 2007126141 A1 * 11/2007

OTHER PUBLICATIONS

Heymann, J. et. al., "Site Specific 3D imaging of cells and tissues with a dual beam microscope." Journal of Structural Biology Jul. 2006, vol. 155, No. 1, pp. 63-73.*

*Primary Examiner* — Jack Berman
*Assistant Examiner* — Wyatt Stoffa
(74) *Attorney, Agent, or Firm* — Polsinelli PC; Teddy C. Scott, Jr.; Ron Galant

(57) ABSTRACT

The invention provides a probe and a method of obtaining a three-dimensional compositional map of one or more targets in a biological sample, or a portion thereof, comprising: (a) milling a surface layer of a biological sample with a focused ion beam, thereby creating a newly exposed surface layer of the biological sample; (b) imaging the newly exposed surface layer of the biological sample; (c) identifying the chemical composition of the newly exposed surface layer of the biological sample, or a portion thereof, with a mass spectrometer; and (d) repeating (a) to (c) until a three-dimensional compositional map of one or more targets in the biological sample, or portion thereof, is obtained. Uses of the three-dimensional map obtained from the inventive method are further provided.

1 Claim, 8 Drawing Sheets

Figure 1:
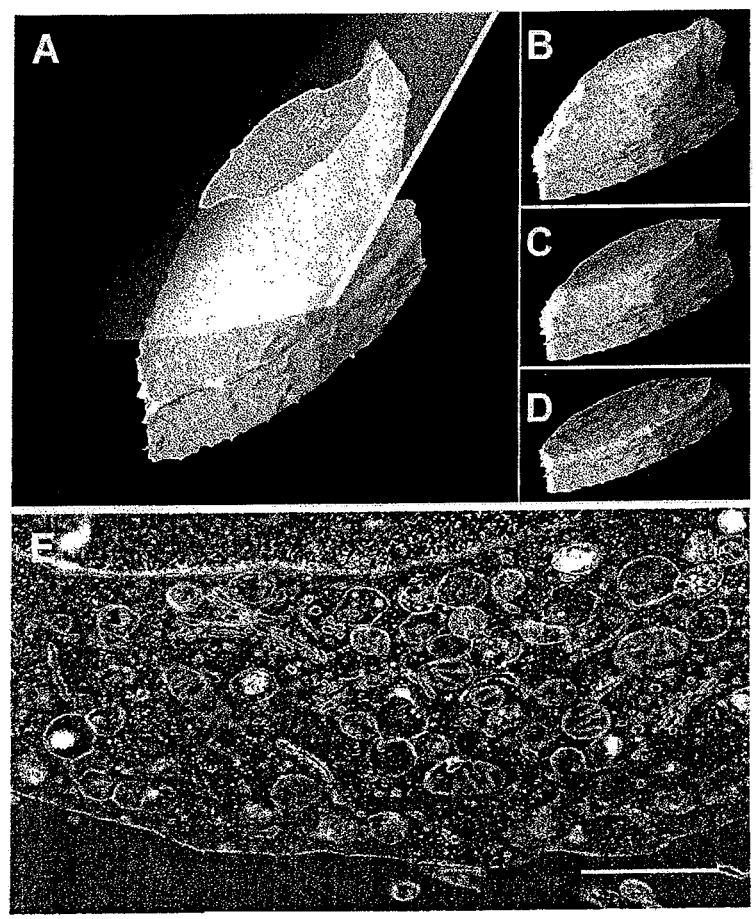

(51) Int. Cl.
*G01N 33/68* (2006.01)
*G01N 33/50* (2006.01)
*H01J 37/28* (2006.01)
*H01J 37/305* (2006.01)
*B82Y 35/00* (2011.01)

(52) U.S. Cl.
CPC ............ *H01J 37/3053* (2013.01); *B82Y 35/00* (2013.01); *H01J 2237/26* (2013.01); *H01J 2237/28* (2013.01); *H01J 2237/31745* (2013.01); *H01J 2237/31749* (2013.01); *H01J 49/0004* (2013.01)
USPC ................ 250/288; 73/866.5; 850/62; 850/5; 250/282

(56) References Cited

U.S. PATENT DOCUMENTS

| | | | | |
|---|---|---|---|---|
| 5,660,181 | A * | 8/1997 | Ho et al. | 600/408 |
| 6,373,665 | B1 * | 4/2002 | Iwamoto | 360/245.9 |
| 6,405,137 | B1 * | 6/2002 | Reading | 702/22 |
| 6,566,653 | B1 * | 5/2003 | Gerber et al. | 250/288 |
| 7,902,499 | B2 * | 3/2011 | Hiraoka et al. | 250/282 |
| 7,910,881 | B2 * | 3/2011 | Nikolaev et al. | 250/288 |
| 2002/0172943 | A1 * | 11/2002 | Henderson et al. | 435/5 |
| 2003/0134273 | A1 * | 7/2003 | Henderson | 435/5 |
| 2003/0193020 | A1 * | 10/2003 | Van Berkel | 250/288 |
| 2004/0051037 | A1 * | 3/2004 | Taylor et al. | 250/288 |
| 2006/0097164 | A1 * | 5/2006 | Knebel et al. | 250/310 |
| 2010/0229263 | A1 * | 9/2010 | Vertes et al. | 850/9 |
| 2011/0031392 | A1 * | 2/2011 | McEwen et al. | 250/283 |
| 2014/0070088 | A1 * | 3/2014 | Otsuka | 250/282 |
| 2014/0070094 | A1 * | 3/2014 | Otsuka | 250/288 |

* cited by examiner

US 8,941,057 B2

PROBE AND METHOD FOR OBTAINING THREE-DIMENSIONAL COMPOSITIONAL MAPS OF A BIOLOGICAL SAMPLE

CROSS-REFERENCE TO RELATED APPLICATIONS

This is the national stage of International Application No. PCT/US2008/075224, which claims the benefit of U.S. Patent Application No. 60/974,686, filed Sep. 24, 2007, and U.S. Patent Application No. 60/970,070, filed Sep. 5, 2007, which are both incorporated by reference.

BACKGROUND OF THE INVENTION

Understanding the hierarchical organization of molecules and organelles within the interior of large mammalian cells is a challenge of fundamental interest in cell biology that may provide fundamental clues to the early detection and treatment of diseases, such as cancer. A wide variety of microscopic and spectroscopic methods already exist for imaging intact cells and their components: modern fluorescence microscopic methods provide versatile tools for imaging the distributions of labeled proteins at spatial resolutions in the micron range, while emerging methods in electron tomography can be used to image the arrangement of protein assemblies at ~5 nm resolution in regions of cells with thicknesses <1 µm. There is, however, a need for technologies that can be used for rapid three-dimensional imaging and compositionally analyzing large mammalian cells.

BRIEF SUMMARY OF THE INVENTION

An embodiment of the invention provides a probe for obtaining a three-dimensional compositional map of one or more targets in a sample, or a portion thereof, the probe comprising (a) a base; and (b) at least one cylindrical extension spatially associated with at least one other cylindrical extension, wherein the cylindrical extensions are attached to the base at one end of the long axis of each of the cylindrical extensions; wherein the spatial association of the cylindrical extensions provides for micron and/or submicron resolution of the sample, or portion thereof, on the three-dimensional compositional map.

Another embodiment of the invention provides a method of obtaining a three-dimensional compositional map of one or more targets in a biological sample, or a portion thereof. An embodiment of the method comprises: (a) milling a surface layer of a biological sample with a focused ion beam, thereby creating a newly exposed surface layer of the biological sample; (b) imaging the newly exposed surface layer of the biological sample; (c) identifying the chemical composition of the newly exposed surface layer of the biological sample, or a portion thereof; and (d) repeating (a) to (c) until a three-dimensional compositional map of one or more targets in the biological sample, or portion thereof, is obtained.

The invention also provides uses of the three-dimensional compositional map obtained from the inventive method.

BRIEF DESCRIPTION OF THE SEVERAL VIEWS OF THE DRAWING(S)

FIGS. 1A to 1D represent the principle of 3D imaging. FIG. 1A represents the use of a focused ion beam moving in the direction of the arrow to expose an interior layer of a cell or tissue specimen, which interior layer is then imaged using scanning electron microscopy. The repetition of exposing and imaging to progress through the cell volume results in a stack of 2D images (examples of which are shown in FIGS. 1B to 1D) that can be combined to generate a 3D representation of the cell.

FIG. 1E represents an image of a cross-section of a cell interior obtained using ion abrasion scanning electron microscopy (IA-SEM), which image illustrates the 2D arrangement of organelles. The scale bar in FIG. 1E is 2 µm.

Figure 1F:
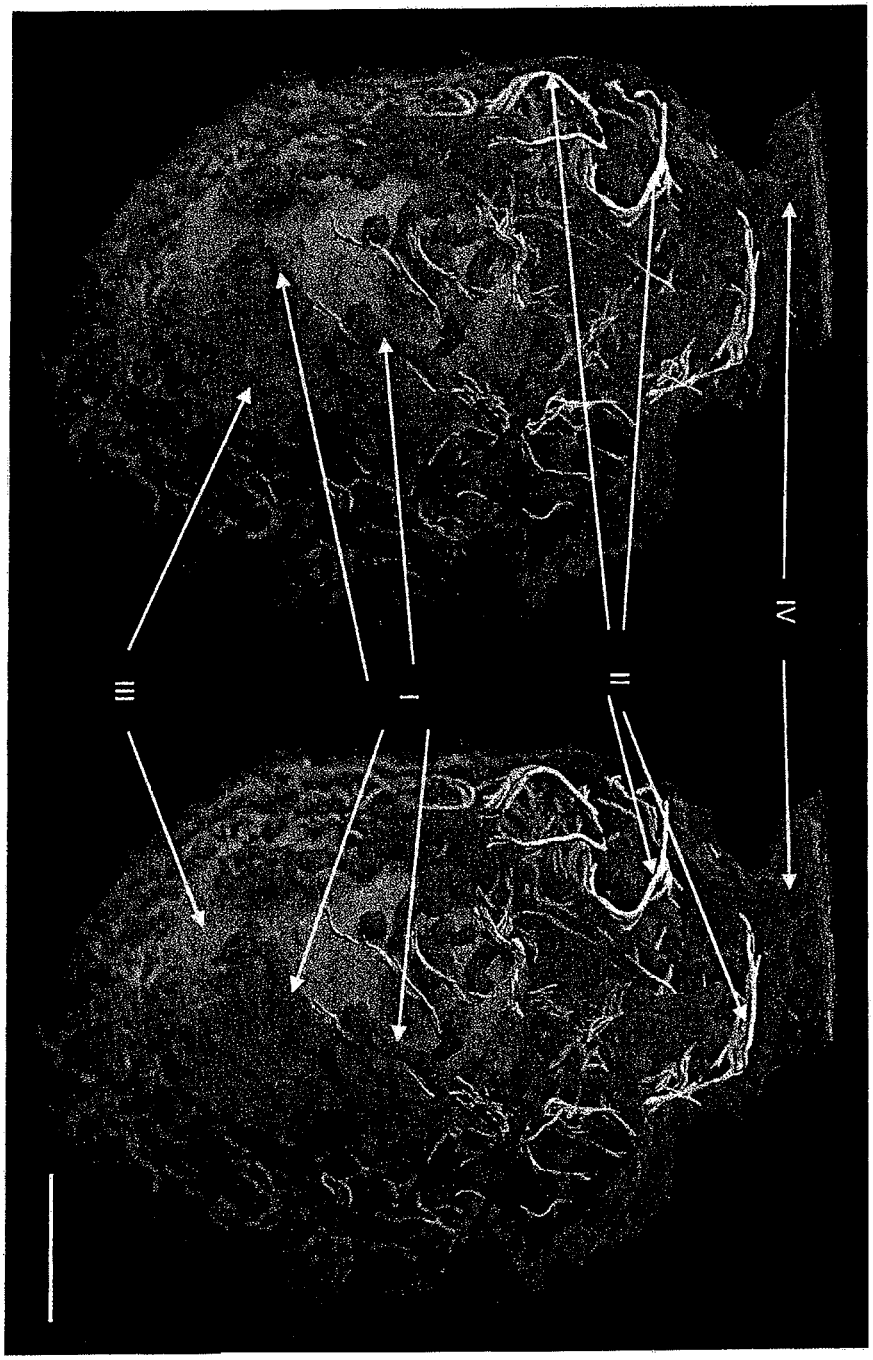

FIG. 1F represents a 3D image of an MNT-1 melanoma cell (~20×35 µm wide) obtained using IA-SEM and segmented to show the spatial arrangement of a selection of mitochondria (Arrow I), endoplasmic reticulum (Arrow II), and the nucleus (Arrow III) relative to the cell envelope (Arrow IV). Inter-image spacing in the stack is ~30 nm, and in-plane pixel size is ~12 nm. The scale bar in FIG. 1F is 10 µm long.

Figure 2:
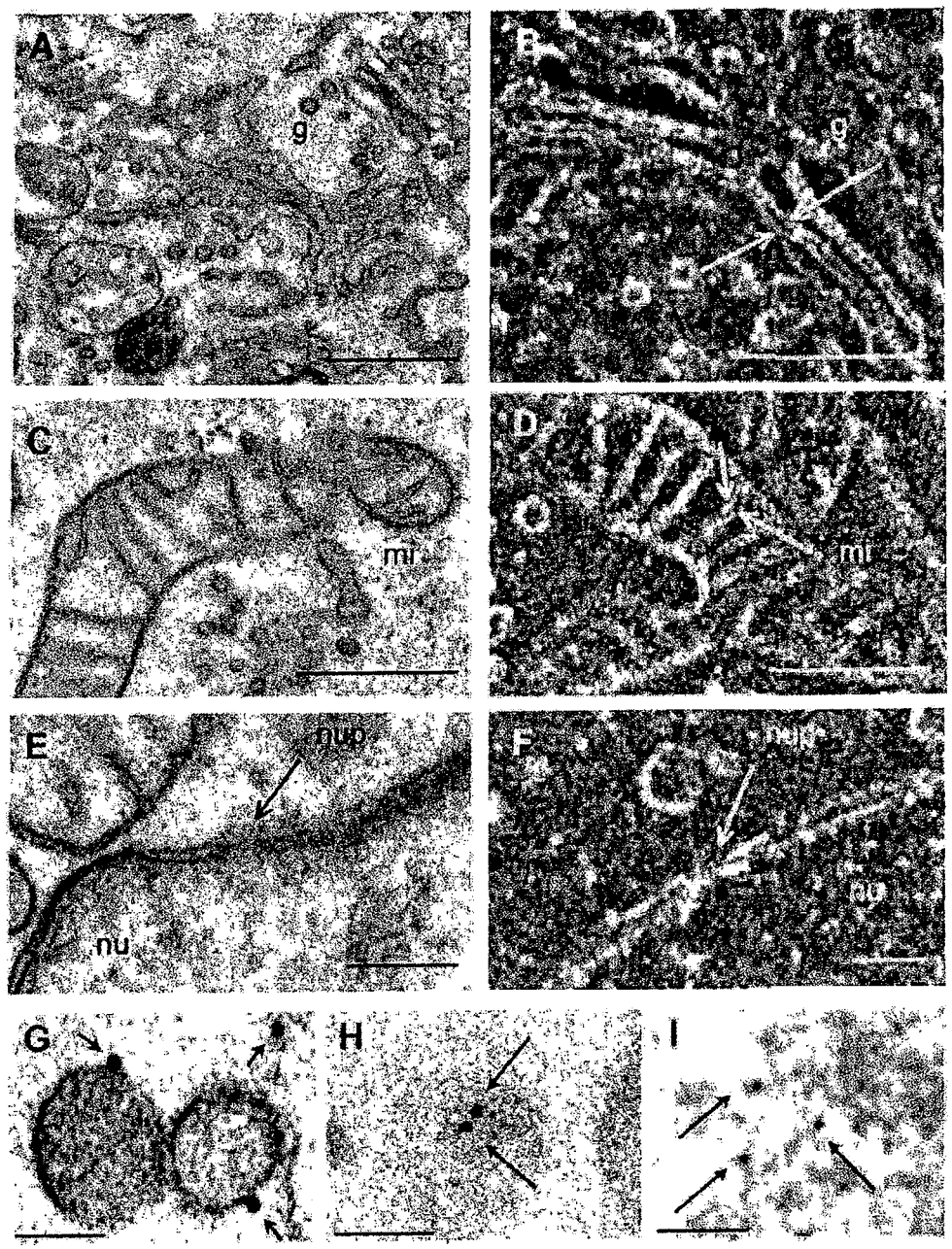

FIG. 2 represents a collection of images depicting image quality and detection of nanoparticle labels in IA-SEM images of MNT-1 melanoma cells. FIGS. 2A to 2F represent a comparative analysis of information present in images of cell interior obtained using conventional TEM (A, C, E) with single slices of similar regions obtained using IA-SEM (B, D, F) at the same pixel size. Arrows indicate details in the membrane organization in mitochondria (mi), Golgi (g), and nuclear pore (nup) in the membrane of the nucleus (nu). (G to I) Detection of 15 nm gold, 10 nm gold conjugated to protein A or quantum dots with 7 nm-size cores (marked by arrows), respectively in individual cross-sectional images from labeled MNT-1 cells. The 15 nm gold and quantum dot particles are taken up passively by the cells, while the protein A-conjugated gold is used to label antibodies specific to the melanoma antigen Pmel17. The images in panels (B, C, D and G to I) are shown with inverted contrast to illustrate similarity in the quality of IA-SEM and TEM images. Inter-image spacing: 20 nm, in-plane pixel size 3.1 nm. Scale bars: (A, B, C, D) 0.5 µm (E, F) 0.2 µm, (G, H, I) 100 nm.

Figure 3:
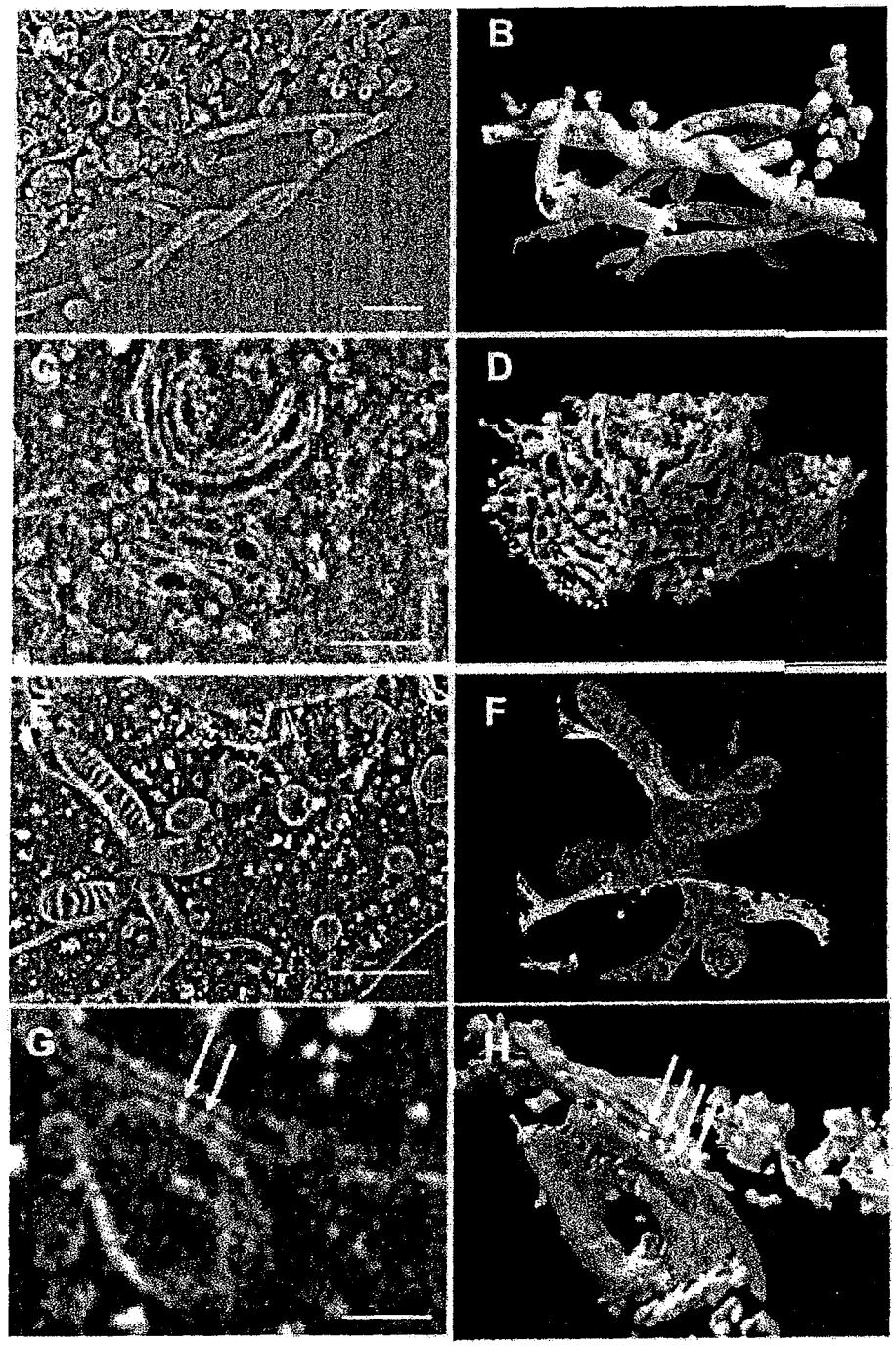

FIG. 3 represents a collection of images which demonstrate the three-dimensional visualization of organelles of MNT-1 melanoma cells using IA-SEM. (A, C, E) Selected 2D images from an image stack obtained by IA-SEM that highlight filopodia (A), Golgi stack (C) and mitochondria with adjacent endoplasmic reticulum (ER) membrane (C). (B, D, F) Rendered 3D volumes derived from the stack of 2D images encompassing the filopodial, Golgi and mitochondrial/ER structures shown in panels A, C and E respectively. FIGS. 3G and 3H represent a close-up view of mitochondria and endoplasmic reticulum bridged by punctate contact regions (shown in white), and indicated by arrows (FIG. 3G). Inter-image spacing: 20 nm, in-plane pixel size 3.1 nm. Scale bars are 1 µm in A, C and E and 100 nm in G.

Figure 4:
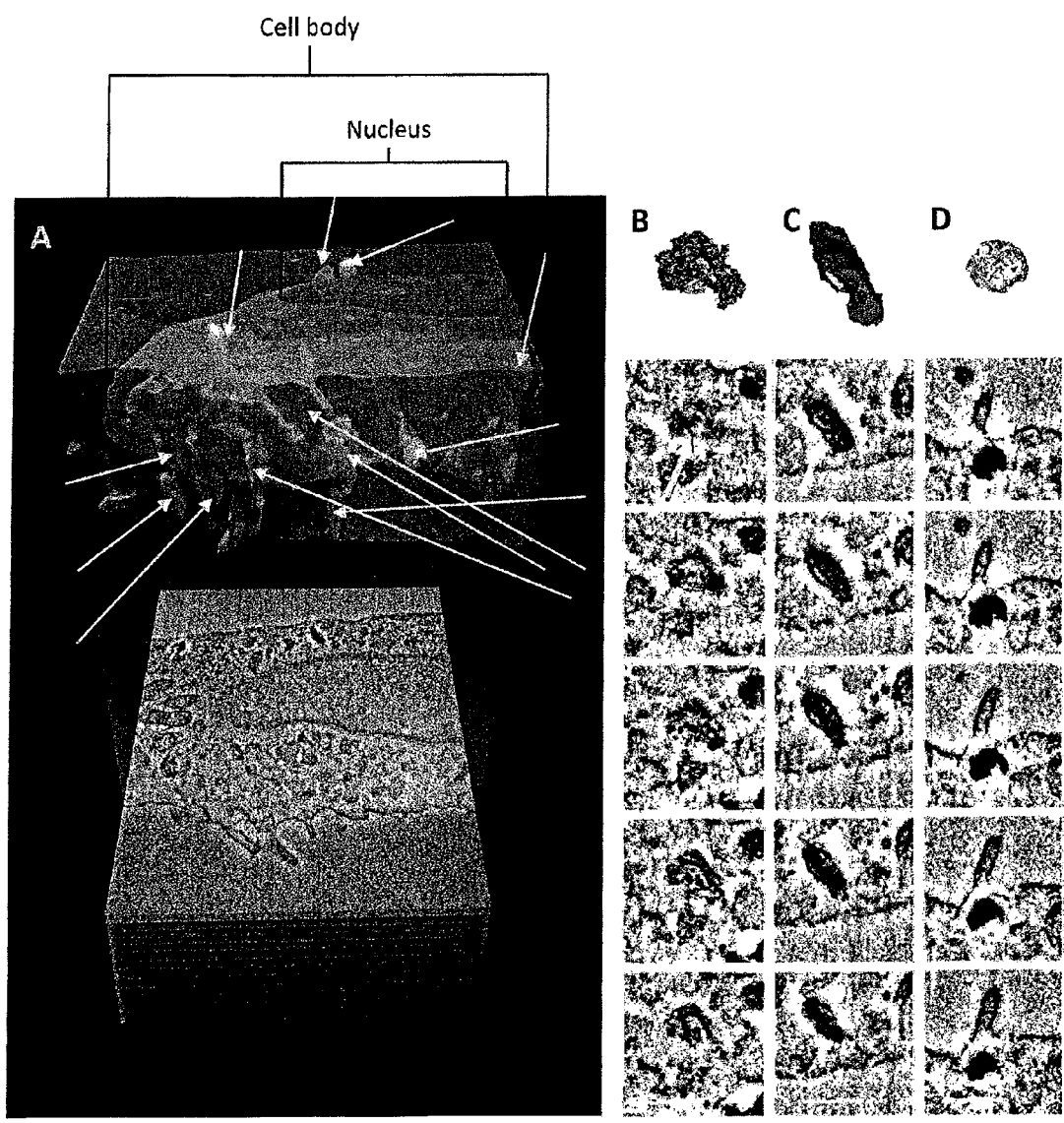

FIG. 4 represents a collection of images demonstrating the detection of melanosome distribution in cultured human melanocytes. FIG. 4A illustrates a segmented 3D representation of an image stack from a cultured melanocyte cell showing the position and distribution of melanosomes (white arrows) within the cell body and outside the nucleus. A single 2D image is shown below the 3D image. FIGS. 4B to 4D represents a set of images showing serial 2D cross-sections of individual segmented melanosomes (indicated by arrows in first row) from FIG. 4A showing differences in internal membrane organization and pigmentation. The melanosome in column (B) has the beginnings of internal membrane organization that is further advanced in the melanosome in column (C), and completed in the melanosome in column (D). Inter-image spacing: 30 nm, in-plane pixel size 6 nm. Scale bars are 0.5 µm in panels in B to D.

Figure 5:
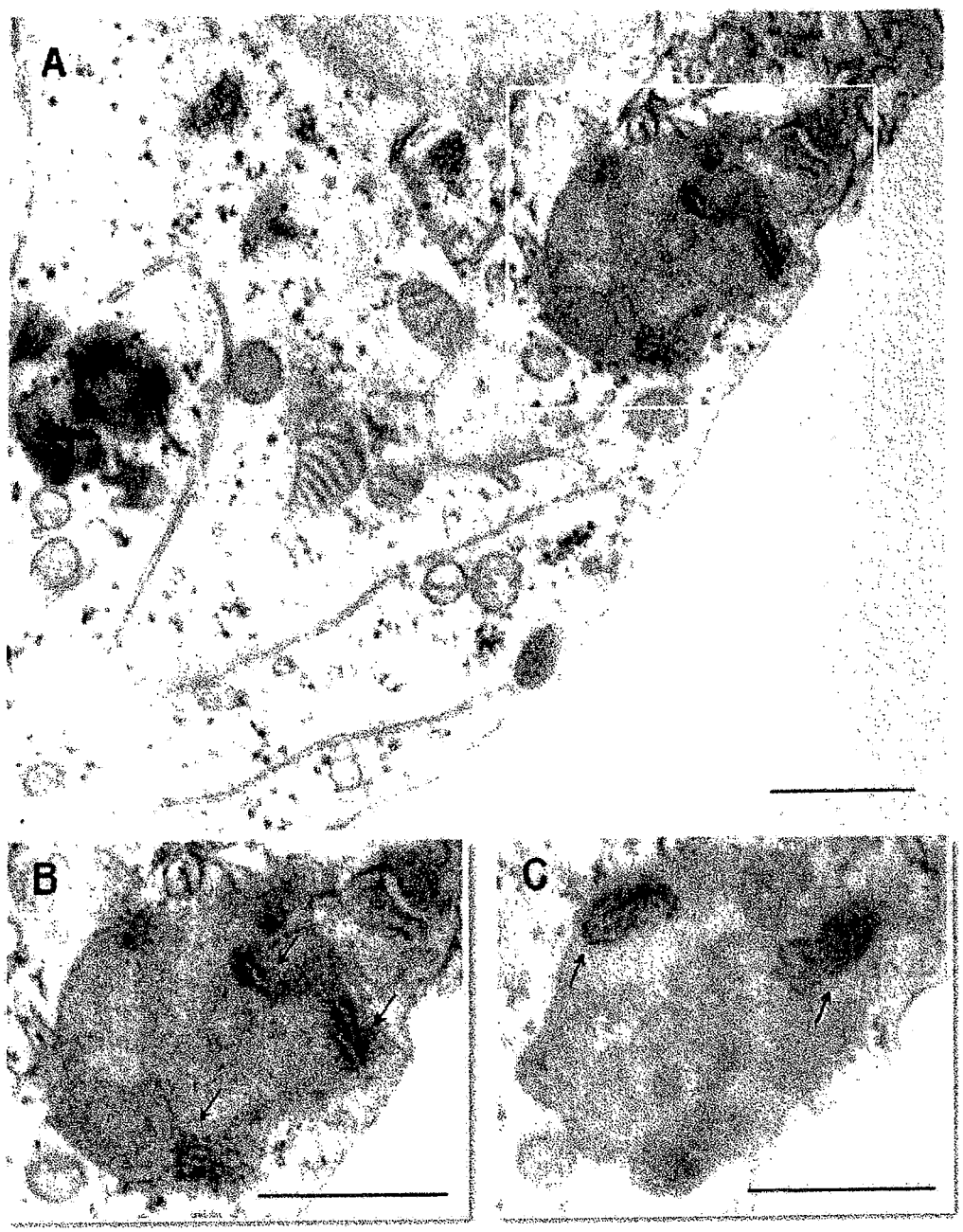

FIG. 5 demonstrates the localization of melanosomes in cultured melanoma cells. A cluster of melanosomes is located in the cell in an area close to the plasma membrane (panel A). The boxed area is shown magnified at two different heights in the imaged volume with arrows pointing to the location of melanosomes (panels B and C). Inter-image spacing: 30 nm, in-plane pixel size 3.1 nm. Scale bar is 1 μm.

Figure 6:

FIG. 6 demonstrates the localization of membrane protrusions in mitochondrial outer membranes. A group of mitochondria is located in a melanoma cell that displayed membrane structures protruding from mitochondria (panel A). The boxed area is show in panel B as a sequence of surface images collected in the process of imaging the cellular volume. Panel C shows another example of a mitochondrion with membrane protrusion found in the same volume. Inter-image spacing: 30 nm, in-plane pixel size 3.1 nm. Scale bar is 1 μm.

Figure 7:
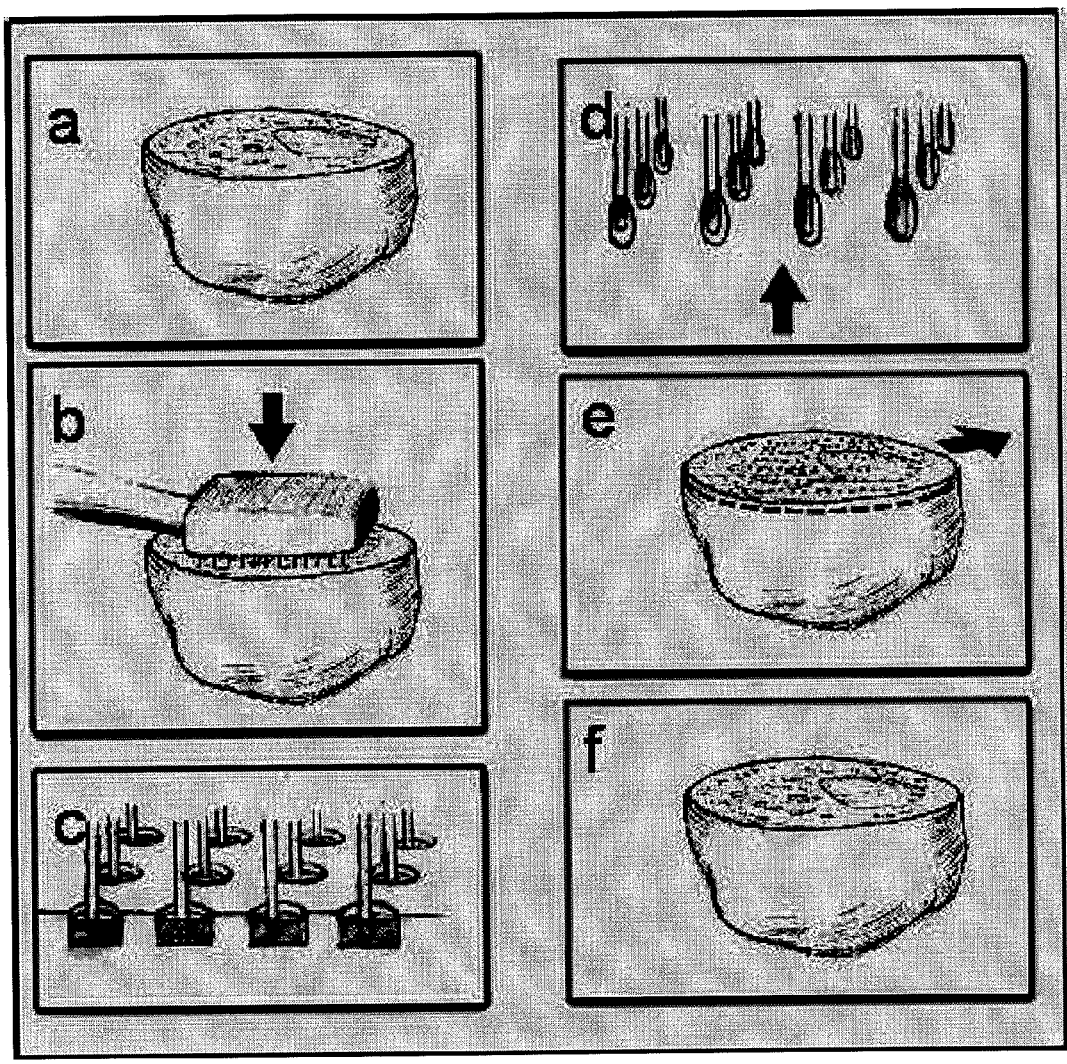

FIG. 7 (panels a to f) is an illustrative diagram representing the use of a probe in obtaining a three-dimensional compositional map, including obtaining a newly exposed surface layer of a biological sample (panel a), contacting the sample with a probe (panels b and c), lifting off the components of the surface layer of the sample (panel d), milling the surface layer of the biological sample (panel d), and obtaining another newly exposed surface layer of a biological sample (panel e).

DETAILED DESCRIPTION OF THE INVENTION

The invention provides a method of obtaining a three-dimensional compositional map of one or more targets in a biological sample. An embodiment of the method comprises: (a) milling a surface layer of a biological sample with a focused ion beam, thereby creating a newly exposed surface layer of the biological sample; (b) imaging the newly exposed surface layer of the biological sample; (c) identifying the chemical composition of the newly exposed surface layer of the biological sample; and (d) repeating (a) to (c) until a three-dimensional compositional map of one or more targets in the biological sample is obtained.

Some embodiments of the method comprise locating one or more targets within the biological sample before identifying the chemical composition of the biological sample or portion thereof with a mass spectrometer. If desired, an embodiment of the method comprises (i) repeating (a) and (b) until the one or more targets is/are locating within the biological sample and (ii) identifying with a mass spectrometer the chemical composition of the biological sample in an area at which the one or more targets is/are located.

In an embodiment, the method comprises (i) gross-milling with a laser, (ii) gross-imaging with a light beam, or (iii) both (i) and (ii), wherein the gross-milling occurs before the milling of (a), wherein the gross-imaging occurs before the imaging of (b). If desired, an embodiment of the method comprises repeating (i) and (ii) until one or more targets is/are located within the biological sample via the gross-imaging.

In accordance with some embodiments of the method, the target is a sub-cellular structure, a biological molecule, an infectious agent, or a pharmaceutical agent. For example, if desired, the one or more targets is/are selected from the group consisting of: a plasma membrane, a nuclear membrane, a nucleus, an endoplasmic reticulum, a golgi body, a cytoskeleton, a protein, a nucleic acid, a lipid, a virus, a bacteria, a drug, and a vector. In some embodiments, the one or more targets is/are labeled with a chemical moiety which is non-native to the biological sample. For example, the chemical moiety can comprise a high atomic weight element, a gold particle, a titanium particle, a fluorophore, an organic compound which is less than 1 kD, or a combination thereof.

Three-Dimensional Compositional Maps

The inventive method ultimately provides a three-dimensional compositional map of one or more targets in a biological sample. As used herein, the term "three-dimensional compositional map" refers to a collection of data points, each data point describing the presence or absence of a target and/or the (relative or absolute) concentration of a target at a specified location within the biological sample. The map comprises several data points, such that the chemical composition at multiple locations of the biological sample is described in this manner.

The method of the invention can be a qualitative method, in which the location(s) of each target, if any, within the biological sample is/are determined. In this regard, the inventive method addresses the questions of whether the target is present in the biological sample and where the target is present in the biological sample.

Alternatively, the method of the invention can be a quantitative method in which the concentration of each target at each location within the biological sample is determined. As mentioned above, the concentration can be an absolute concentration (e.g., an exact copy number of a nucleic acid target or a molar amount of a protein target), or a relative concentration (e.g., amount of one target expressed relative to the amount of another target).

The three-dimensional compositional map obtained by the inventive method can include varying amounts of information (i.e., of data points), such that the three-dimensional compositional map can be a fine map comprising several thousand data points or a gross map comprising less data points. As one of ordinary skill in the art can appreciate, the inventive method in which a gross map is obtained takes less time than the method in which a fine map is obtained. Therefore, the method of the invention can advantageously be tailored, e.g., as desired to the ultimate application of the map.

Biological Samples

As used herein, the term "biological sample" is meant any sample or specimen comprising one or more cells, e.g., prokaryotic and/or eukaryotic cells, or a portion thereof. The biological sample can be a single cell, or a portion thereof, or a (homogenous or heterogeneous) population of cells. The biological sample alternatively can be a tissue or a portion thereof. Suitable biological samples for purposes herein include, but are not limited to, biological fluid samples (e.g., whole blood, serum, plasma, interstitial fluid, lymph, saliva, semen, milk), whole cells (e.g., whole mammalian or plant cells) or a fraction thereof (e.g., a cryostat), cell populations (e.g., cell cultures and cells from, for example, a leukopheresis), and tissues (e.g., tissue from a biopsy, a diseased or injured tissue).

The biological sample can be obtained from any source. For example, the biological sample can be a cell or tissue obtained from a host, wherein the host can be any of the hosts described herein. As further elaborated upon herein below, the biological sample can be obtained from a healthy or diseased host, such that the three-dimensional composition map obtained can serve as a diagnostic or prognostic tool.

Alternatively, the biological sample can be a synthetic or artificially-made biological sample, e.g., an engineered cell, cell culture, or tissue, or a cell, cell culture, or tissue that has been treated with a pharmaceutical agent.

For purposes herein, the biological sample can be a liquid biological sample or a solid biological sample. Preferably, the biological sample is a solid biological sample. More preferably, the biological sample is a frozen biological sample or a cryopreserved biological sample. Most preferably, the biological sample is a cryopreserved biological sample.

Targets

The term "target" as used herein refers to any chemical or biochemical entity on which the inventive method provides information (e.g., the presence/absence, the concentration, location within the biological sample). The target can be, for example, a subcellular structure (e.g., a plasma membrane, a nuclear membrane, a nucleus, an endoplasmic reticulum, a golgi body, a cytoskeleton, a cytoplasm), a biological molecule (a protein, a nucleic acid, a lipid), an infectious agent (a virus, a bacteria, a parasite), or a pharmaceutical agent (a small molecular weight compound, a peptide, a vaccine, a vector). The target also can be an allergen, a toxin, a metabolite, and the like. In this regard, the target can be a chemical or biochemical entity which is endogenous or exogenous to the cell(s) of the biological sample.

In one embodiment of the invention, the target(s) is/are labeled with a chemical moiety which is non-native (i.e., exogenous) to the biological sample and which is not chemically identical to the target itself. The chemical moiety label facilitates the imaging of the target(s) within the biological sample. Suitable chemical moieties for purposes herein include, for example, an element particle (e.g., a gold particle, a titanium particle, a high atomic weight element particle (e.g., a lanthanide)), a fluorophore (e.g., fluorescein isothiocyanate (FITC), phycoerythrin (PE)), a radioisotope, an organic compound which is preferably less than 1 kilodaltons (e.g., a ketone), or a combination thereof. See, for instance, Gronemeyer et al., *Curr. Opin. Biotech.* 16: 453-458 (2005).

Alternatively, the target can be devoid of any chemical moiety (label). Rather, the target can be located based on the properties of the target itself. For example, if the target is a subcellular structure, e.g., the endoplasmic reticulum, the target can be located through identifying its shape. Alternatively, the target can be devoid of any chemical moiety (label), but its binding partner is labeled with the chemical moiety. In this instance, the binding partner of the target is located before identifying the chemical composition of the target.

With respect to the inventive method, there can be one or more targets. For instance, there can be 1, 2, 3, 4, 5, 10, 25, or more different targets. Preferably, when more than one target is mapped, each target is labeled with a chemical moiety that is unique to the target. For example, the method can comprise obtaining a three-dimensional compositional map of two targets, wherein one target is labeled with a lanthanide ion and the other is labeled with a gold particle.

The chemical moieties can be directly attached to the target (or binding partner thereof) or can be attached to the target (or binding partner thereof) via a linker, provided that the chemical moiety or linker, once attached to the target (or binding partner thereof), does not interfere with the function of the target (or binding partner thereof). Also, the attachment of the chemical moiety or linker to the target (or binding partner thereof) can be a covalent attachment or a non-covalent attachment, e.g., an electrostatic attachment, a hydrophobic interaction, etc. Suitable linkers are known in the art and include, for example, a peptide fusion tag (e.g., a tetracysteine tag, which binds to biarsenical compounds, a lanthanide binding tag, etc.), a ligand (e.g., an oligohistidine tag, which reversibly binds to nitrilotriacetate derivatives; an alkylated $O^6$-alkylguanine-DNA alkyltransferase), an antibody (e.g., a gold-labeled secondary antibody), or antigen binding portion thereof, or a combination thereof. See, for instance, Martin et al., *J. Am. Chem. Soc.* 129: 7106-7113 (2007) and Gronemeyer et al., 2005, supra. The linker also can be, for example, a binding partner of the target.

In the instance that the linker is a peptide fusion tag, the peptide fusion tag preferably binds to a high atomic weight element, such as a lanthanide ion. In this regard, the peptide fusion tag preferably is a lanthanide binding tag, such as those described in Martin et al., 2007, supra, Franz et al., *ChemBioChem* 4: 265-271 (2003); and Nitz et al., *ChemBioChem* 4: 272-276 (2003). Also preferred is for the target to be genetically engineered as a fusion protein comprising the peptide fusion tag and for the cell(s) of the biological sample to express the fusion protein comprising the target and peptide fusion tag. See, Martin et al., 2007, supra, MacKenzie et al., *Immunotechnology* 1: 139-150 (1995); and Vazquez-Ibar et al., *Proc. Natl. Acad. Sci. U.S.A.* 99: 3487-3492 (2002).

In another preferred embodiment, the peptide fusion tag binds to an organic compound which is less than 1 kilodalton, e.g., a ketone, a heterocyclic compound, a nitrilotriacetate, or a derivative thereof, a biarsenical fluorophore, a benzylguanine, and an aliphatic halogenated compound. As for any of the chemical moieties and linkers described herein, the organic compound preferably is relatively chemically inert, such that the presence of the organic compound inside the cell of the biological sample will not interfere with the function of the cell or any components thereof. Suitable peptide fusion tags which specifically bind to an organic compound of less than 1 kD are known. See, for example, Gronemeyer et al., 2005, supra.

The peptide fusion tag also can be one which is designed and selected via a screening method in which several peptides are screened for the ability to specifically bind to a particular chemical moiety. Such screening methods are known in the art and include, for example, a combinatorial screening of peptide libraries (Martin et al., *QSAR Comb. Sci.* 24: 1149-1157 (2005)) or a phage display screening method. Such methods of designing and selecting suitable peptide fusion tags are generally known in the art. See, for example, Nitz et al., 2003, supra.

Milling a Surface Layer

The inventive method of obtaining a three-dimensional composition map comprises milling a surface layer of a biological sample to create a newly exposed surface layer of the biological sample. By "milling" as used herein refers to the removal of a portion of a biological sample from the sample. The milled surface layer can be essentially of any thickness, provided that the thickness is only a fraction of the thickness of the entire biological sample being mapped, since the method comprises repeatedly milling the surface layer of the biological sample. Because a focused ion beam can be used to mill a very thin layer (e.g., about 20 to about 200 nm) of a biological sample, the milling is accomplished with a focused ion beam, when milling a surface layer of a biological sample to create a newly exposed surface layer of the biological sample.

The focused ion beam can comprise any type of ion, such as, for instance, gallium ions, bucky ball (C60+) ions, cesium, ions, oxygen ions, bismuth ions, and the like. Such focused ion beams, as well as the use thereof for milling, are well-known in the art. See, for instance, Tomiyasu et al., *Secondary Ion Mass Spectrometry, SIMS*12, Benninghoven et al., eds. Elsevier (2000) 473; Hayles et al., *J. Microsc.* 226 (Pt. 3): 263-269 (2007); Xiong et al., *Applied Physics Letters* 79: 3461-3463 (2001); and Woldering et al., Nanotechnology 17: 5717-5721 (2006); Prenitzer et al., *Microsc. Microanal.* 9: 216-236 (2003); and Cheng et al., *J. Am. Soc. Mass Spectrom.* 18: 406-412 (2007).

When milling a surface of the biological sample, the focused ion beam can be moved across the biological sample in a single plane in a horizontal direction. Such milling can be considered as planar milling. Alternatively, the focused ion beam can be moved vertically and horizontally across the surface layer of the biological sample. For example, the focused ion beam can be moved across the biological sample, such that one or more hills or surface protrusions are formed on the surface layer of the biological sample. Such milling can be considered as pattern milling, since, in most cases, the hills or surface protrusions on the surface layer forms a pattern. An array of surface protrusions can be formed via the pattern-milling. Alternatively, the hills or surface protrusions may not create a regular pattern. Rather, the surface protrusions may form a random pattern.

Imaging the Surface Layer

The inventive method comprises imaging the newly exposed surface layer (created by the milling) of the biological sample. The imaging can be accomplished through any means of imaging the biological sample, provided that the imaging produces cellular or sub-cellular images. Such imaging techniques are known in the art and include, for example, fluorescent microscopy, confocal microscopy, electron tomography, transmission electron tomography, immuno-electron microscopy, large-area atomic force microscopy, and scanning electron microscopy. Preferably, the imaging is accomplished with a scanning electron beam, i.e., the imaging is performed via scanning electron microscopy, such as the imaging described herein below as Example 1.

Identifying the Chemical Composition of the Surface Layer

The inventive method further comprises identifying the chemical composition of the biological sample (or portion thereof). Identifying the chemical composition of the surface layer can comprise identifying the chemical composition of only the targets of the biological sample. Thus, for example, when the target is a mitochondrion, the identifying can comprise identifying the chemical composition of one or more components, preferably each component found within the mitochondrion. In another embodiment of the invention, the identifying can comprise identifying the chemical composition of the binding partners of the target(s) and/or can comprise the identification of the chemical composition of an area in which the target(s) is/are located. The inventive method can advantageously be suited to any of these purposes.

Identifying the chemical composition of the surface layer can be accomplished by any means. Preferably, the chemical composition is identified with a mass spectrometer, operated singly or in tandem, although other means do exist. The mass spectrometer can be any type of mass spectrometer, provided that the mass spectrometer provides the chemical composition of the biological sample. In a preferred embodiment of the invention, the mass spectrometer is a mass spectrometer in which the mobile phase is a liquid, i.e., the mass spectrometer is a liquid phase mass spectrometer. Alternatively, the mass spectrometer can be a secondary ion mass spectrometer.

Identifying the chemical composition of the surface layer can be accomplished by means other than mass spectrometry. For example, RT-PCR can be used to identify the chemical composition of the surface layer of the biological sample, if the three-dimensional compositional map is to map one or more nucleic acids. For example, the target can be the mRNAs located in the cytoplasm of the cell and the method comprises identifying the chemical composition of the mRNAs through RT-PCR. Also, as discussed herein below, the method can comprise the use of a microarray, which serves as both a probe and a means of identifying the chemical composition of the surface layer of the biological sample. Furthermore, identification may or may not include amplification. For example, use of amplification such as PCR to amplify nucleic acids in the sample, to facilitate, e.g., sequencing of the nucleic acids, may be employed.

Whole vs. Portion of Biological Sample and Repeated Cycles

The inventive method comprises repeating the milling, imaging, and identifying until a three-dimensional compositional map of the one or more targets in the biological sample (or portion thereof) is obtained. In one embodiment of the invention, the method comprises a cycle of milling, imaging, and identifying at each exposed surface layer until the entire biological sample is mapped. Preferably, the map thus obtained provides the location of one or more components of the biological sample at one or more locations of the biological sample.

In some instances, the three-dimensional compositional map of the entire biological sample is unnecessary and/or undesired. The task of obtaining such a composition map can, for example, be too time-consuming for the ultimate purpose of the three-dimensional compositional map. In such cases, the method can comprise milling, imaging, and identifying until only a portion of the biological sample is mapped. For instance, if the target is a nucleus of a mammalian cell and the biological sample is the mammalian cell, the milling, imaging, and identifying can be repeated until only the portion of the cell containing the nucleus is mapped. Such methods that comprise mapping only a portion of the biological sample can comprise one or more cycles of gross-milling and/or fine-milling combined with gross-imaging and/or fine-imaging, as further discussed herein below.

The method of the invention can comprise locating the one or more targets within the biological sample before identifying the chemical composition of the surface layer of the biological sample. Locating the one or more targets can be accomplished through one or more cycles of gross-milling and/or fine-milling combined with gross-imaging and/or fine-imaging. As used herein, the term "gross-milling" refers to the milling of a thick layer of the biological sample (e.g., a layer which is about 10 microns or greater). As used herein, the term "fine-milling" refers to the milling of a thin layer of the biological sample (e.g., about 20 nm to about 200 nm). Generally, the fine-milling is accomplished with a focused ion beam, while the gross-milling is achieved with an optical laser. However, the gross-milling can also be accomplished with a focused ion beam.

In this regard, the method can comprise repeated cycles of milling with a focused ion beam and imaging with a scanning electron beam until one or more targets are located within the biological sample (and before identifying the chemical composition of the surface layer of the biological sample). The imaging and milling cycles can further comprise gross-imaging in combination with the fine-imaging and/or gross-milling in combination with fine-milling. Preferably, the gross-milling occurs before the fine-milling (e.g., milling with a focused ion beam) and the gross-imaging occurs before the fine-imaging (e.g., the imaging with the scanning electron beam). For instance, the method can comprise repeated cycles of gross-milling with an optical laser and gross-imaging with a light beam until one or more targets are located, followed by one or more cycles of milling with a focused ion beam, imaging with a scanning electron beam, and identifying the chemical composition of the newly exposed surface layer of the biological sample. The method can subsequently comprise further cycles of gross-imaging and gross-milling, if, for example, the following two or more surface layers milled and imaged revealed the absence of any targets.

Liquid Phase MS

As mentioned above, the mass spectrometer used to identify the chemical composition of the surface layer of the biological sample can be a liquid phase mass spectrometer. In such an instance, the method can, for example, comprise (a) milling a surface layer of a biological sample with a focused ion beam, thereby creating a newly exposed surface layer of the biological sample; (b) imaging the newly exposed surface layer with a scanning electron beam; (c) positioning a probe over the newly exposed surface layer; (d) contacting the probe with the newly exposed surface layer, thereby lifting off components of the surface layer onto the probe; (e) optionally transferring the components of the surface layer from the probe into a receiving unit; (f) identifying the chemical composition of the components on the probe or in the receiving unit optionally with the mass spectrometer; and (g) repeating (a) through (f) until a three-dimensional compositional map of one or more targets in the biological sample or portion thereof is obtained.

Lifting Off—Probe and Receiving Unit

As used herein, the term "lifting off" refers to the transfer of one or more components from an original surface to a second surface in a manner which preserves the relative position of each of the components of the original surface onto the second surface. For purposes herein, the components of the surface layer of the biological sample are lifted off from the surface layer of the biological sample onto a surface of the probe (e.g., as represented in FIG. 7d), such that the relative position of each of the components is preserved when transferred onto the surface of the probe.

The term "probe" as used herein refers to any object which can be precisely positioned over a surface layer and can contact the sample for purposes of lifting off the components of the surface layer of the sample (e.g., as represented in FIGS. 7b and 7c). Suitable probes include, for example, a brush comprising one or more bristles, a probe comprising a flat surface, or a microarray (e.g., a DNA chip, a protein chip). The probe can comprise any suitable type(s) of materials, such as silicon, plastic, glass, a polymer (e.g., nitrocellulose, polyvinylidene fluoride, metal (e.g., a conducting metal, e.g., copper, titanium, nickel).

A preferred embodiment of the invention is a probe for obtaining a three-dimensional compositional map of one or more targets in a sample, or a portion thereof, the probe comprising (a) a base; and (b) at least one cylindrical extension spatially associated with at least one other cylindrical extension, wherein the cylindrical extensions are attached to the base at one end of the long axis of each of the cylindrical extensions; wherein the spatial association of the cylindrical extensions provides for micron and/or submicron resolution of the sample, or portion thereof, on the three-dimensional compositional map. Such a probe comprises two or more cylindrical extensions, or "prongs," e.g. bristles of a brush, placed in predetermined spatial arrangements to provide particular three-dimensional compositional maps, depending upon the desired application and/or sample, or portion thereof. Additionally or alternatively, the prongs/bristles may be of differing lengths along the long axis of the cylinders, providing for the simultaneous sampling of differing depths. The base of the probe may be in contact with a positioning device. Such a device may allow for micron and/or submicron movement of the probe.

The probe may be used, for example, with a sample of a thin film, a biological sample, or a pharmaceutical formulation. The embodiments of the probe and methods of the invention may be used to determine, e.g., the chemical composition of thin films as various layers of the films are being deposited. This would be useful, for example, when the evenness of the film layers is important or for confirming deposition of particular patterns of molecules. Another example of a sample is a pharmaceutical formulation. For example, determination of a three-dimensional compositional map of a pharmaceutical agent within a sustained- or controlled-release matrix formulation would be helpful in efforts to further control the release profile of the pharmaceutical agent.

The lifted off components on the probe can be transferred to a receiving unit. The term "receiving unit" as used herein refers to any object which can receive each of the lifted off components on the surface of the probe in a manner which preserves the relative position of each of the lifted off components. In one embodiment of the invention, the probe is a brush comprising an array of bristles and the receiving unit is an array of wells or capillaries. Each well or capillary fits a bristle of the brush and the array of wells or capillaries thereby preserves the relative position of each of the lifted off components (e.g., the bristles including the lifted off components shown in FIG. 7d can be inserted into the wells of a multiwall plate). Such receiving units are known in the art. See, for instance, Kang et al., *Anal. Chem.* 77: 6243-6249 (2005)).

In some instances, a receiving unit is unnecessary. For example, if the probe is a nitrocellulose membrane, then the identification of the chemical composition of the lifted off components can be accomplished without transferring the components from the nitrocellulose membrane. Also, for instance, if the target is the nucleus of the cell and the probe is a DNA microarray, then the components of the surface layer of the biological sample need not be transferred from the probe to a receiving unit. In such an instance, identifying the chemical composition with a mass spectrometer may be unnecessary as well, since the DNA microarray can identify the components of the nucleus (target).

Alternatively, the probe can be a probe comprising a flat surface, e.g., a silicon probe. In this instance, the method can comprise, for example, (a) pattern-milling a surface layer of a biological sample with a focused ion beam, thereby creating a patterned surface comprising at least one surface protrusion; (b) imaging the patterned surface with a scanning electron beam; (c) positioning the probe comprising a flat surface over the patterned surface; (d) contacting the flat surface of the probe with the patterned surface, thereby lifting off components of the patterned surface at each surface protrusion onto the flat surface of the probe; thereby creating a spot comprising the components of the patterned surface on the flat surface of the probe for each surface protrusion of the patterned surface; (e) identifying the chemical composition of the components of the patterned surface with a mass spectrometer for each spot; (f) milling at least a portion of each surface protrusion of the patterned surface with a focused ion beam; (g) repeating (a) through (f) until each surface protrusion has been completely milled down, thereby creating a flat surface of the biological sample; and (h) repeating (a) through (g) until a three-dimensional compositional map of one or more targets in the biological sample or portion thereof is obtained. In a preferred embodiment of the invention, the patterned surface comprises an array of surface protrusions.

To facilitate the lifting off process, the method can comprise the application of heat or an electric field to the probe before contacting the probe with the newly exposed surface. Alternatively or additionally, the method can comprise applying heat or an electric field to the probe at the same time the probe is contacting the newly exposed surface. The heat or electric field can conceivable make the components of the biological sample more amenable to being lifted off. For example, if the biological sample is a frozen sample and the probe is a brush with multiple bristles, the method can comprise heating the bristles of the brush, so that the heated bristles can melt into the surface layer of the frozen biological sample so that the resulting liquid components adhere to the bristles via electrostatic interactions.

As mentioned above, it is necessary for proper lifting off that the probe is precisely positioned or maneuvered over the newly exposed surface layer. Means of precisely positioning the probe are known in the art. For example, the probe can be positioned over the newly exposed surface with a piezoelectric device or a cantilever, e.g., a nanocantilever. Such devices are known in the art. For example, such devices are manufactured by Omniprobe (Dallas, Tex.).

Tryptic Digestion

The method of the invention can comprise any standard use of the mass spectrometer, including, for example, the use of a mass spectrometer to identify the chemical composition upon the tryptic peptides of the chemical components. In this respect, the method can comprise (i) digesting the components in the receiving unit with trypsin, thereby obtaining tryptic peptides, (ii) identifying the chemical composition of the peptides with a mass spectrometer, and (iii) comparing the chemical composition of the tryptic peptides to known tryptic peptide fingerprints. The term "known tryptic peptide fingerprints" as used herein refers to any of the published tryptic peptide fingerprints, including, for example, those found in the Swiss Prot database or GenBank database, which known tryptic peptide fingerprints can be screened using the Aldente peptide mass fingerprinting tool available on the Expert Protein Analysis System (ExPasy) website.

SIMS

The mass spectrometer can be a secondary ion mass spectrometer (SIMS). SIMS is well-known in the art. See, for example, Chapter 13 of Giannuzzi and Stevie, eds., *Introduction to Focused Ion Beams, Instrumentation, Theory, Techniques and Practice*, Springer, 2005, which chapter is entitled "Focused Ion Beam Secondary Ion Mass Spectrometry (FIB-SIMS)." In this instance, the method can comprise (a) planar-milling a surface layer of a biological sample with a focused ion beam, thereby creating a newly exposed surface and milled components of the biological sample; (b) detecting the secondary ions of the milled components of the biological sample in real-time with the planar-milling with a secondary ion mass spectrometer, thereby positionally identifying the chemical composition of the milled components; (c) imaging the newly exposed surface; and (d) repeating (a) through (c) until a three-dimensional compositional map of one or more targets in the biological sample or portion thereof is obtained.

Device

The invention further provides a device which enables the production of a three-dimensional compositional map of a biological sample in accordance with the method of the invention. The device comprises a source of a focused ion beam for milling a biological sample, a scanning electron microscope for imaging the surface layer of the biological sample, and a mass spectrometer. The source of a focused ion beam can any focused ion beam tool, such as, for example, a V600FIB (FEI Company, Hillsboro, Oreg.) or a VectraVision™ (FEI Company). The scanning electron microscope can be any such as, for instance, Inspect S™ or Inspect F™ scanning electron microscope (FEI Company) or a JSM-7000F (JEOL, Tokyo, Japan). The mass spectrometer can be any mass spectrometer, such as a liquid phase mass spectrometer or a secondary ion mass spectrometer. The mass spectrometer can be, for example, a Microflex™, Microflex LT™, Autoflex II™, or Esquire6000™ (Bruker Daltonics Inc., Billerica, Mass.) or a AccuTOF™ API-TOF LC/MS system (JEOL, Tokyo, Japan). The device can further comprise any one or more of a stage for holding a biological sample, a light microscope (e.g., a fluorescence microscope), an optical laser, a piezoelectric device and/or cantilever for positioning a probe over the biological sample. The stage can be a stage which allows the environment of the biological sample to be controlled. For instance, the stage can be a stage which can control the temperature of the biological sample or can control the amount of $CO_2$ in the environment of the biological sample.

Applications of Three-Dimensional Compositional Maps

The three-dimensional compositional map can be used to diagnose or prognose a disease or condition in a host. In this regard, the invention provides a method of diagnosing or prognosing a disease or condition in a host. The method comprises (i) obtaining a three-dimensional compositional map of one or more targets of a biological sample of the host in accordance with any of the methods of obtaining a three-dimensional compositional map described herein, wherein the one or more targets are characteristic of the disease or condition, and (ii) comparing the three-dimensional compositional map of the target(s) of the biological sample of the host to a control three-dimensional compositional map of the target(s).

For example, the disease can be a cancer which is characterized by the loss of expression of a particular protein in a specific part of a cell, e.g., the nucleus. In this regard, a three-dimensional compositional map of the host exhibiting a loss of this protein in the nucleus is indicative of the host having the cancer. Alternatively, some cancers are characterized by overexpression of a particular protein; and in this case, a three-dimensional compositional map exhibiting increased expression of the particular protein indicates that the host has cancer. Loss of expression and/or overexpression may be unique to a particular protein, a particular tissue, and/or a particular developmental stage of a cell. Therefore, a three-dimensional compositional map may be generated using different biological samples and/or different targets to determine if a host has one or more types of cancer.

Furthermore, the disease can be, for instance, an autoimmune disease which is characterized by an interaction of two proteins. In this case, a three-dimensional compositional map of the host exhibiting the interaction is indicative of the host having the autoimmune disease.

The disease referred to herein can be any disease, e.g., an infectious disease, an autoimmune disease, a cancer. For purposes herein, "infectious disease" means a disease that can be transmitted from person to person or from organism to organism, and is caused by a microbial agent (e.g., common cold). Infectious diseases are known in the art and include, for example, hepatitis, sexually transmitted diseases (e.g., *Chlamydia*, gonorrhea), tuberculosis, HIV/AIDS, diphtheria, hepatitis B, hepatitis C, cholera, and influenza.

For purposes herein, "autoimmune disease" refers to a disease in which the body produces an immunogenic (i.e., immune system) response to some constituent of its own tissue. In other words the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

As used herein, the term "condition" as used herein can be any type of state of being, such as a state of development (e.g., embryonic, aging), a wounded or injured condition or a healing condition, a predisposition to any of the diseases described herein, any medical condition or syndrome, including, for example, a disorder, allergy, inflammation, high cholesterol, high blood pressure, migraine headaches, fever, eczema, and the like.

The host referred to herein can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Alternatively, the three-dimensional compositional map can be used to determine the treatment regimen for a host afflicted with a disease or a condition. For example, if the host has breast cancer, a three-dimensional compositional map of the estrogen receptor (ER) of breast tissue from the host can indicate that the host would respond to certain types of chemotherapy, e.g., tamoxifen.

The three-dimensional compositional map can be used to address the identification of binding partners of a particular pharmaceutical agent, as well as localize the pharmaceutical agent. In this respect, the invention also provides a method of identifying the binding partners of a particular pharmaceutical agent. The method comprises (i) obtaining a three-dimensional compositional map of a biological sample of a host treated with the pharmaceutical agent in accordance with any of the methods of obtaining a three-dimensional compositional map described herein and (ii) identifying the chemical composition of the biological sample in the vicinity of the pharmaceutical agent.

As used herein, the term "pharmaceutical agent" refers to any agent administered to one or more cells (e.g., a tissue, a host) for purposes of treating or preventing a disease or condition. The pharmaceutical agent can be a small molecule (e.g., a synthetic organic compound), a nucleic acid (e.g., a gene therapy vector, miRNA), a peptide or protein (e.g., a peptide vaccine, a monoclonal antibody), or a derivative thereof (e.g., a peptidomimetic)

The following examples further illustrate the invention but, of course, should not be construed as in any way limiting its scope.

EXAMPLES

Example 1

This example demonstrates a method of milling with a focused ion beam and imaging with a scanning electron beam.

Plastic embedded melanoma and melanocyte cells are prepared as follows: Cells from the human melanoma cell line, MNT-1, or melanocyte cultures (obtained from Dr. Vincent Hearing, NCI Bethesda, Md.) are grown on 10 cm culture dishes at 37° C., 10% $CO_2$ in DMEM medium (Invitrogen, Carlsbad, Calif.) containing 10% fetal bovine serum (Hyclone, Logan, Utah), 1% L-Glutamine (Invitrogen) and 1% penicillin/streptomycin (Invitrogen) to about 70% confluence. For plastic embedding, cells are fixed with 2.5% glutaraldehyde in 0.1 M cacodylate (pH 7.2) at room temperature followed by osmication using reduced, aqueous osmium tetroxide (2% osmium tetroxide, 1.5% $Fe(II)(CN)_6 2H_2O$). Cells are then mechanically dislodged and processed for conventional embedding in EMBed-812 (EMS, Hatfield, Pa.) following the supplier's protocol. For uptake experiments, cells are grown under standard conditions to about 70% confluence. QuantumDot conjugate (7 nm core, Invitrogen) or 15-nm BSA-gold (EMS, Hatfield, Pa.) is first pre-bound to cells at 4° C. for 10 min and uptake is then induced by incubation for 30 min at 37° C. Cells are processed for TEM and SEM analysis as described below. For pre-embedding immunolabeling with a polyclonal anti-Pmel17 antibody (McIntosh et al., *Trends Cell. Biol.* 15: 43-51 (2005)) specific for the C-terminal region (αPEP13h), MNT-1 cells are grown as described below after seeding on glass chamber slides. At about 70% confluence, cells are incubated with paraformaldehyde (4% in 0.1 M cacodylate buffer) overnight. Excess aldehyde is quenched with 35 mM glycine-permeabilized with 0.5% Triton X-100 for 5 min at room temperature. Prior to antibody labeling, cells are treated with 1% fish-gelatin, 0.1% saponin to minimize non-specific binding.

Ion-abrasion SEM procedures are carried out as follows: Resin blocks are physically processed as described (Subramaniam, *Curr. Opin. Microbiol.* 8, 316-322 (2005)). Prior to IA-SEM analysis, specimen quality is inspected routinely by TEM imaging. For this purpose, 70-nm to 100 nm sections are prepared by microtome sectioning, collected on carbon-coated 200 mesh copper grids, and stained for 5 min with 2% aqueous uranyl acetate, followed by staining for 2 min with 1 mM lead citrate. Images are collected at 120 kV (Tecnai 12, FEI) using a 2 k×2 k CCD camera (Gatan, Pleasanton, Calif.). Once specimen quality is verified, tailored block surfaces are coated with platinum-palladium, and mounted on the stage of a Nova 200 Nanolab (FEI Eindhoven, NL). On a selected area, typically a ~1 μm layer of platinum is deposited using a gas injector system in the main specimen chamber to provide a smooth, conducting surface. Cross-sections are prepared using the focused ion beam (gallium source) at 30 kV and beam currents ranging between 0.5 nA and 3.0 nA. Secondary electron scanning images are typically recorded at accelerating voltages of 3 to 5 kV in the immersion lens mode, using an Everhard-Thornley detector. 2D image stacks are acquired using the 'slice-and-view' imaging module (FEI) and nominal inter-image distances are set to the desired values ranging from 10 nm to 200 nm.

2D SEM image stacks are registered either by using ImageJ in conjunction with specific plugins or aligned by using the IMOD software suite (McIntosh, *Cellular Electron Microscopy*, Methods in Cell Biol. (Academic Press, 2007)). Images are bandpass-filtered to sharpen membrane contours and imported either into IMOD or Amira (Mercury Computer Systems, Inc., Chelmsford, Mass.) for segmentation and rendering.

The principle of obtaining three-dimensional (3D) images of cellular specimens by iterating application of the focused ion beam (Giannuzzi and Stevie, 2005, supra) with imaging using a scanning electron beam is shown in FIGS. 1A to D. A focused gallium ion beam is used to abrade the surface of the block in areas typically ~40 μm×~40 μm in step sizes of ~20 nm. Each newly exposed surface is imaged with the scanning electron beam, with acquisition times ranging from 60-160 seconds per image, depending on the pixel size used. A successive stack of 3D images can therefore provide an informative 3D map of the three-dimensional distribution of cellular organelles. Using this strategy, aldehyde-fixed, osmium-stained, plastic-embedded MNT-1 melanoma cells are imaged. A representative example of the type of information about mitochondrial and endomembrane architecture that can routinely be obtained using IA-SEM in 2D and in semi-automatically segmented 3D images are shown respectively in FIGS. 1E and 1F.

In FIGS. 2A to 2F, a detailed comparison of images of the cell interior acquired using ion abrasion scanning electron microscopy (IA-SEM; FIGS. 2B, 2D, 2F) with TEM imaging of ~80 nm thin sections (FIGS. 2A, 2C and 2E) prepared from the same block is presented. Key ultra-structural features such as the Golgi, mitochondria and the locations of the nuclear pore complex can be visualized in each IA-SEM image slice with clarity that is comparable to that expected in conventional TEM images. Closely apposed membranes in the Golgi stack (~20 nm apart) as well as the spacing of the invaginated mitochondrial inner membrane (~12 nm apart), and the spacing of the lipid bilayer membrane of inner and outer nuclear membranes (~6 nm) can be resolved in single IA-SEM images. In addition to describing sub-cellular architecture at each abraded plane, IA-SEM can also be combined with pre-embedding immunolabeling, providing a powerful tool for combined 3D antigen localization and sub-cellular imaging at nanometer resolution. It is shown that polyclonal antibodies that recognize the C-terminal region of the melanoma antigen Pmel17 (Valencia et al., *J. Cell. Sci.* 119, 1080-1091 (2006)) can be located using protein-A conjugated with 10 nm-sized gold (FIG. 2H) to the cytoplasm. In parallel experiments, 15 nm-sized colloidal gold particles are added to evaluate passive gold uptake, and it is shown that they can be detected at the surface of the filopodial membranes (FIG. 2G). Thus, specific labeling with differently sized gold particles effectively allows mapping pair-wise protein proximities in 3D. Yet another avenue for labeling is afforded by the fact that quantum dot particles with 7-nm sized cores can be recognized (FIG. 2I), suggesting the effectiveness of combining lower resolution fluorescence microscopic imaging with higher resolution IA-SEM imaging.

The use of IA-SEM in accordance with an embodiment of the invention provides for rapid 3D imaging of the cellular interior to reveal structural detail that cannot easily be deduced from 2D projection images alone. Three examples are presented in FIG. 3, illustrating how 3D imaging at 20 nm resolution (with in-plane pixel size of 3.1 nm) provides valuable information on the interdigitated architecture of filopodia at the cell surface (FIGS. 3A, B), the branched structure of a Golgi body (FIGS. 3C, D) and the convoluted arrangement of mitochondria (FIG. 3E, F). The ability to rapidly image these shapes in 3D provides a powerful starting point for quantitative understanding of cell architecture. For example, automated segmentation of mitochondria in MNT-1 cells allows extraction of estimates for metrics such as the volume of cytoplasm occupied by mitochondria (~5%), difference between surface area of inner vs. outer membranes (~2-fold), and mean mitochondrial width (~450 nm). The 3D images also reveal the unique complementarity in curvature between the mitochondria and the closely associated endoplasmic reticulum membrane, and provide experimental measures of curvature that could be important information for efforts aimed at computational modeling of mitochondrial function (Balaban, *Am. J. Physiol. Cell Physiol.* 291, C1107-C1113 (2006)) and its changes over different cellular states (Birkedal et al., *Am. J. Physiol. Cell Physiol.* 291, C1148-C1158 (2006)). Yet another insight from the images is the glimpse of densities at the contact zones (FIGS. 3G, H) between mitochondria and the endoplasmic reticulum. The existence of physical links or "tethers" between these two organelles has been shown in previous TEM analyses of isolated mitochondrial and endoplasmic reticulum preparations (Csordas et al., *J. Cell Biol.* 174, 915-921 (2006); Meier, M. A. Spycher, U. A. Meyer, *Biochim. Biophys. Acta.* 646, 283-297 (1981)). The use of IA-SEM combined with immunolabeling of protein complexes such as IP3 receptors and VDAC proteins may help further elucidate the structural role of the complexes formed by association of these and other proteins (Szabadkai et al., *J. Cell Biol.* 175, 901-911 (2006)) postulated to form a $Ca^{++}$ tunnel between mitochondria and endoplasmic reticulum (Rapizzi et al., *J. Cell Biol.* 159, 613-624 (2002)). The 3D images presented here are the first direct observation of the three-dimensional interface between these two organelles in a whole cell.

Using strategies established for investigating MNT-1 melanoma cells, IA-SEM is used to image human melanocytes (FIG. 4) in an ongoing effort to better understand structural mechanisms underlying skin pigmentation and the potential subcellular origins of skin cancer. Melanin is produced in small organelles known as melanosomes that are transferred by an as yet unknown mechanism from melanocytes to the surrounding keratinocytes (Van Den Bossche et al., Traffic 7, 769-778 (2006)). The arrival of melanosomes in keratinocytes is central to their normal function. Numerous diseases leading to abnormal pigmentation such as Hermansky-Pudlak syndrome, Chediak-Higashi syndrome in which patients have compromised immune system function have been documented (Van Den Bossche, 2006, supra). While many of the molecules that are important for the process have been identified (Dell'Angelica, *Curr. Opin. Cell Biol.* 16, 458-464 (2004)), central questions that remain unanswered include knowledge of the intracellular distribution of melanosomes at different stages of biogenesis (Kushimoto et al., *Proc. Natl. Acad. Sci. U.S.A.* 98, 10698-10703 (2001)), and the types of mechanisms that could be involved in melanin transfer. Here it is shown that not only can the 3D melanosome distribution be determined using IA-SEM (FIG. 4a), but differential staining of individual melanosomes, which corresponds to variations in melanin accumulation, can be identified. The 3D images demonstrate that the melanosomes are not bounded by membranes in these melanocytes in contrast to the compartmentalized "bags" of melanosomes observed in MNT-1 melanoma cells (FIG. 5) The melanoma cells also show other unusual features such as protrusions of the outer mitochondrial membrane (FIG. 6) that, together with knowledge of the spatial distribution and extent of staining could provide new opportunities to define structural signatures associated with normal and cancerous cells.

The spatial resolution achieved using IA-SEM exceeds that reported to date by all other approaches for 3D imaging of the interior of mammalian cells such as X-ray tomography (Gu et al., *Differentiation* 75, 529-535 (2007)), optical microscopy (Egner et al., *J. Struct. Biol.* 147, 70-76 (2004)), confocal scanning transmission electron microscopy (Einspahr and Voyles, *Ultramicroscopy* 106, 1041-1052 (2006)) and block-face scanning electron microscopy (21), which combines the use of a microtome with scanning electron microscopy. In contrast to sectioning with a microtome, the use of a focused ion beam allows repetitive removal of material with high precision (typically <0.5% variation from one cut to the next in our experience) with virtually none of the problems associated with microtome-based sectioning such as mass loss between successive slices, or cutting artifacts induced by surface defects in the diamond or glass knives. As currently implemented, IA-SEM is immediately applicable to imaging plastic-embedded cell and tissue specimens of the kind routinely used in clinical settings, and will closely complement newly emerging tools for higher resolution fluorescence microscopic imaging that exploit photo-activatable probes (Betzig et al., *Science* 313, 1642-1645 (2006)).

This example demonstrated a strategy for 3D imaging of biological specimens which combines iterative removal of material from the surface of a bulk specimen using focused ion beam milling with imaging of the newly exposed surface using scanning electron microscopy (Heymann et al., *J. Struct. Biol.* 155, 63-73 (2006)). Using this experimental approach, that is termed ion abrasion scanning electron microcopy (IA-SEM), large mammalian cells are rapidly imaged at resolutions of ~20-nm in the z-direction (direction of section removal), and ~6 nm in the x-y plane (plane of section removal). Individual gold and quantum dot particles can be localized in the images, demonstrating that IA-SEM is a powerful method for obtaining combined information on 3D ultrastructure and molecular localization.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of obtaining a three-dimensional compositional map of one or more targets in a biological sample comprising one or more cells, or a portion thereof, comprising:
   (a) milling a surface layer of a biological sample with a focused ion beam thereby creating a newly exposed surface layer of the biological sample;
   (b) imaging the newly exposed surface layer of the biological sample;
   (c) positioning a probe over the newly exposed surface layer, the probe comprising:
      (i) a base; and
      (ii) at least one cylindrical extension spatially associated with at least one other cylindrical extension, wherein the cylindrical extensions are attached to the base at one end of the long axis of each of the cylindrical extensions;
   wherein the spatial association of the cylindrical extensions provides for micron and/or submicron resolution of the sample, or portion thereof, on the three-dimensional compositional map;
   (d) contacting the probe with the newly exposed surface layer, thereby lifting off components of the surface layer onto the probe;
   (e) optionally transferring the components of the surface layer from the probe into a receiving unit;
   (f) identifying the chemical composition of the components on the probe or in the receiving unit with the mass spectrometer; and
   (g) repeating (a) to (f) until a three-dimensional compositional map of one or more targets in the biological sample, or portion thereof, is obtained.

* * * * *